(12) United States Patent
Kahn et al.

(10) Patent No.: US 10,463,300 B2
(45) Date of Patent: Nov. 5, 2019

(54) BODY-WORN MONITOR

(71) Applicants: Philippe Kahn, Santa Cruz, CA (US); Arthur Kinsolving, Santa Cruz, CA (US)

(72) Inventors: Philippe Kahn, Santa Cruz, CA (US); Arthur Kinsolving, Santa Cruz, CA (US)

(73) Assignee: DP TECHNOLOGIES, INC., Scotts Valley, CA (US)

( * ) Notice: Subject to any disclaimer, the term of this patent is extended or adjusted under 35 U.S.C. 154(b) by 9 days.

(21) Appl. No.: 13/622,325

(22) Filed: Sep. 18, 2012

(65) Prior Publication Data

US 2013/0072765 A1    Mar. 21, 2013

Related U.S. Application Data

(60) Provisional application No. 61/536,532, filed on Sep. 19, 2011.

(51) Int. Cl.
| | |
|---|---|
| *G06F 1/3206* | (2019.01) |
| *A61B 5/00* | (2006.01) |
| *A61B 5/01* | (2006.01) |
| *A61B 5/11* | (2006.01) |

(52) U.S. Cl.
CPC ............ *A61B 5/681* (2013.01); *A61B 5/01* (2013.01); *A61B 5/11* (2013.01); *A61B 5/4815* (2013.01); *G06F 1/3206* (2013.01); *A61B 5/0002* (2013.01); *A61B 5/4839* (2013.01); *A61B 2560/0209* (2013.01)

(58) Field of Classification Search
CPC .... A61B 2560/0209; A61B 2560/0242; A61B 2560/0252; A61B 5/01; A61B 5/0002; A61B 5/0008; A61B 5/11; A61B 5/681; A61B 5/4815; A61B 5/4839; A61B 5/6824; A61B 5/6828; A61B 5/6831
USPC .................. 600/300, 301, 483; 340/573.1
See application file for complete search history.

(56) References Cited

U.S. PATENT DOCUMENTS

| | | | |
|---|---|---|---|
| 5,928,133 | A | 7/1999 | Halyak |
| 6,348,694 | B1 | 2/2002 | Gershteyn et al. |
| 6,888,779 | B2 | 5/2005 | Mollicone et al. |

(Continued)

FOREIGN PATENT DOCUMENTS

| | | |
|---|---|---|
| EP | 1139187 B1 | 10/2001 |
| WO | WO 2005/092177 | 10/2005 |

(Continued)

OTHER PUBLICATIONS

Plarre et al., "Autiomated Detection of Sensor Detachements for Physiological Sensing in the Wild", Wireless Health' 10 Oct. 5-7, 2010.*

(Continued)

*Primary Examiner* — Boniface N Nganga
(74) *Attorney, Agent, or Firm* — HIPLegal LLP; Judith Szepesi

(57) ABSTRACT

In one embodiment, the system is a body-worn device comprising an accelerometer and a temperature sensor. The system in one embodiment includes a power management system to move the body-worn device into a low power state when the body-worn device is not being worn, the power management system determining when the body-worn device is worn based on a combination of sensor data.

20 Claims, 13 Drawing Sheets

(56) References Cited

U.S. PATENT DOCUMENTS

| | | | |
|---|---|---|---|
| 8,398,546 B2 | 3/2013 | Pacione et al. | |
| 8,770,742 B2 | 7/2014 | Howell et al. | |
| 8,793,212 B2 | 7/2014 | McGuire | |
| 8,840,564 B2 | 9/2014 | Pinhas et al. | |
| 9,192,326 B2 | 11/2015 | Kahn et al. | |
| 2004/0049132 A1 | 3/2004 | Barron et al. | |
| 2004/0075549 A1* | 4/2004 | Haller | 340/522 |
| 2004/0133081 A1 | 7/2004 | Teller et al. | |
| 2004/0149921 A1 | 8/2004 | Smyk | |
| 2004/0152957 A1 | 8/2004 | Stivoric et al. | |
| 2005/0143617 A1 | 6/2005 | Auphan | |
| 2005/0154330 A1 | 7/2005 | Loree, IV | |
| 2005/0172311 A1* | 8/2005 | Hjelt et al. | 725/10 |
| 2005/0245839 A1 | 11/2005 | Stivoric et al. | |
| 2005/0264752 A1 | 12/2005 | Howell et al. | |
| 2006/0202816 A1* | 9/2006 | Crump | A61B 5/02055 340/539.12 |
| 2006/0293608 A1 | 12/2006 | Rothman et al. | |
| 2007/0018832 A1 | 1/2007 | Beigel et al. | |
| 2007/0186330 A1 | 8/2007 | Howell et al. | |
| 2008/0052837 A1 | 3/2008 | Blumberg | |
| 2008/0117060 A1 | 5/2008 | Cuddihy et al. | |
| 2008/0122616 A1 | 5/2008 | Warner et al. | |
| 2008/0234785 A1 | 9/2008 | Nakayama et al. | |
| 2008/0234935 A1* | 9/2008 | Wolf et al. | 701/216 |
| 2008/0275349 A1 | 11/2008 | Halperin et al. | |
| 2008/0306351 A1 | 12/2008 | Izumi | |
| 2009/0069642 A1* | 3/2009 | Gao | A61B 5/02055 600/300 |
| 2009/0147215 A1 | 6/2009 | Howell et al. | |
| 2009/0203971 A1* | 8/2009 | Sciarappa | G08B 21/0453 600/301 |
| 2010/0049008 A1 | 2/2010 | Doherty et al. | |
| 2010/0056947 A1* | 3/2010 | Holmes | A61B 5/7267 600/549 |
| 2010/0079294 A1 | 4/2010 | Rai et al. | |
| 2010/0100004 A1 | 4/2010 | Someren | |
| 2010/0283616 A1* | 11/2010 | Ruhs et al. | 340/573.1 |
| 2010/0306711 A1* | 12/2010 | Kahn et al. | 715/863 |
| 2011/0010014 A1 | 1/2011 | Oexman et al. | |
| 2011/0015467 A1 | 1/2011 | Dothie et al. | |
| 2011/0015495 A1 | 1/2011 | Dothie et al. | |
| 2011/0092780 A1* | 4/2011 | Zhang et al. | 600/301 |
| 2011/0152637 A1* | 6/2011 | Kateraas et al. | 600/301 |
| 2011/0190594 A1 | 8/2011 | Heit et al. | |
| 2011/0270052 A1* | 11/2011 | Jensen et al. | 600/302 |
| 2011/0298613 A1* | 12/2011 | Ben Ayed | 340/539.11 |
| 2012/0103556 A1 | 5/2012 | Lee | |
| 2012/0221254 A1* | 8/2012 | Kateraas et al. | 702/19 |
| 2012/0313272 A1* | 12/2012 | Fullam | B29C 45/1671 264/36.1 |
| 2012/0316471 A1 | 12/2012 | Rahman et al. | |
| 2012/0316932 A1* | 12/2012 | Rahman | G06Q 50/22 705/14.1 |
| 2012/0317430 A1* | 12/2012 | Rahman | G06F 1/3296 713/323 |
| 2013/0018284 A1 | 1/2013 | Kahn et al. | |
| 2013/0072765 A1 | 3/2013 | Kahn et al. | |
| 2013/0124891 A1 | 5/2013 | Donaldson | |
| 2014/0018686 A1* | 1/2014 | Medelius et al. | 600/483 |
| 2014/0259433 A1 | 9/2014 | Nunn et al. | |
| 2014/0277822 A1 | 9/2014 | Nunn et al. | |
| 2015/0083934 A1 | 3/2015 | Richter | |

FOREIGN PATENT DOCUMENTS

| | | |
|---|---|---|
| WO | WO 2006/009830 | 1/2006 |
| WO | WO 2008/072168 | 6/2008 |
| WO | 2011161680 A2 | 12/2011 |

OTHER PUBLICATIONS

Coyle, Shirley, et al, "Textile Sensors to Measure Sweat pH and Sweat-rate During Exercise," <http://doras.dcu.ie/3636/1/Coyle_pervasive2009.pdf>, Accessed Sep. 12, 2012, 6 pages.

"Direct Link Between Insulin, Core Body Temperature Discovered," Thaindian News, <http://www.thaindian.com/newsportal/health/direct-link-between-insulin-core-body-temperature-discovered_100277502.html>,Nov. 20, 2009, 3 pages.

"Metabolic Temperature Graph," Dr. Rind, <http://www.drrind.com/therapies/metabolic-temperature-graph>, Accessed Sep. 18, 2012, 5 pages.

"Monitoring Disparities in Chronic Conditions Study: The MDCC Study," <http://www.healthmetricsandevaluation.org/research/project/monitoring-disparities-chronic-conditions-study-mdcc-study>, Accessed Sep. 7, 2012, 2 pages.

PCT/US12/56146, International Preliminary Report on Patentability, dated Feb. 6, 2014, 19 pages.

"SunMate Ultraviolet Light Intensity Meter," <http://www.natures-energies.com/uv_meter.htm#.UIpCP44qe-ghat>, Accessed Oct. 26, 2012, 1 page.

"UV Sunsignals Sensors," <http://sunsignals.com/how-it-works/> Accessed Oct. 26, 2012, 2 pages.

PCT/US2012/056146, International Search Report and Written Opinion, dated Mar. 7, 2013, 19 pages.

PCT/US2012/056146, Invitation to Pay Additional Fees and, Where Applicable, Protest Fee, dated Jan. 2, 2013, 7 pages.

PCT/US/2012/056146, International Preliminary Report on Patentability (Jun. 2, 2014) (17 pages).

Iber, Conrad et al; The AASM manual for the Scoring of Sleep and Associated Events: Rules, Terminology and technical Specification, 1st ed., 2007 American Academy of Sleep medicine, Westchester, Illinois.

* cited by examiner

BODY-WORN MONITOR

RELATED CASES

The present invention is related to, and claims the benefit of the filing date of U.S. Provisional Application No. 61/536,532, filed on Sep. 19, 2011. The provisional application is incorporated herein in its entirety.

FIELD

The present invention is related to body-worn monitors, and more particularly to a body-worn monitor including a plurality of sensors.

BACKGROUND

As medicine advances, and sensors are miniaturized, sensors targeted to consumers are increasingly available. Pedometers based on accelerometer or other motion sensors are becoming more common.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

Figure 1A:
FIGS. 1A-1C are diagrams of embodiments of a body-worn monitor that includes the present invention.

An improved body-worn monitor including a plurality of sensors is described. In one embodiment, the body-worn monitor is a wristband. For simplicity, the term "wristband" is used herein to refer to a body-worn monitor, though one should understand that the body-worn monitor might be worn elsewhere. For example, the body-worn monitor may be worn as an arm band, leg strap, chest strap, hat, glasses, head band, integrated in a garment worn on the body, or in another format. In one embodiment, the body-worn device is in physical contact with the users body at least periodically.

In one embodiment, wristband includes an accelerometer or similar motion sensing apparatus, a temperature sensor, and may include one or more other sensors such as gyroscope(s), heart monitors, pressure sensors, and others. The sensors, in one embodiment, may be used for monitoring the user's activity, sleep, and health. In one embodiment, the sensors may be used for power management of the wristband. In one embodiment, the wristband may also include user interface features such as a display, one or more LED or other light sources, a vibration system, a push button, a selection knob, or another way for the user to interact with the wristband directly. In one embodiment, the wristband may be used to monitor a medical condition and provide useful feedback and prompting to the user. The medical condition may be a chronic condition such as diabetes or heart disease, which may be addressed by the user with or without the use of medications.

In one embodiment, the wristband may be coupled to a computer system such as a mobile device, a laptop, or desktop computer, or a remote server system. In one embodiment, the wristband may further connect to another output device, e.g. a Bluetooth headset, wired headset, speaker system, etc. The device to which the wristband is coupled may provide user interface and control features in one embodiment. In one embodiment, the system is designed to have the wristband provide a minimal communication and control functions directly, while features that are more complex are provided through the additional output device or computer system. In one embodiment, the sensor data collected from the user is merged, in the computer system. The merging, in one embodiment, integrates the sensor data into the historical data set, and enables the integration of data from additional sources as well. The computer system may be receiving data from multiple wristbands, external sensors, other user monitoring systems, or manual input from the user. Using the received data, in one embodiment, the system ensures that only sensor data from a worn-device is used by the system.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional, and other changes may be made without departing from the scope of the present invention. The following detailed description is, therefore, not to be taken in a limiting sense, and the scope of the present invention is defined only by the appended claims.

Figure 1B:
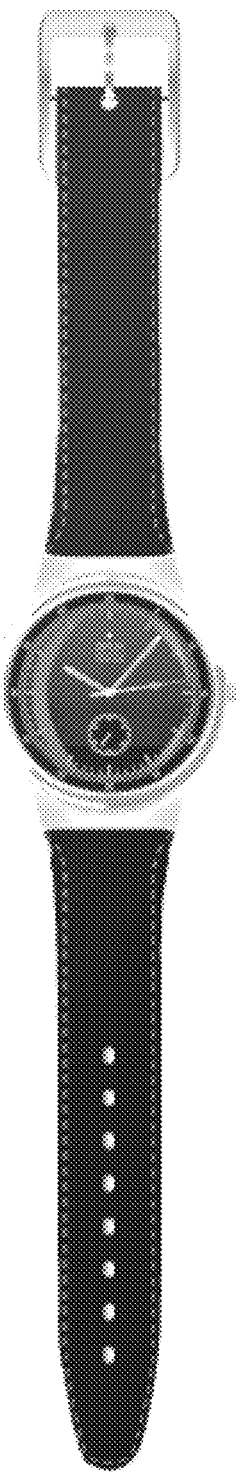
Figure 1C:
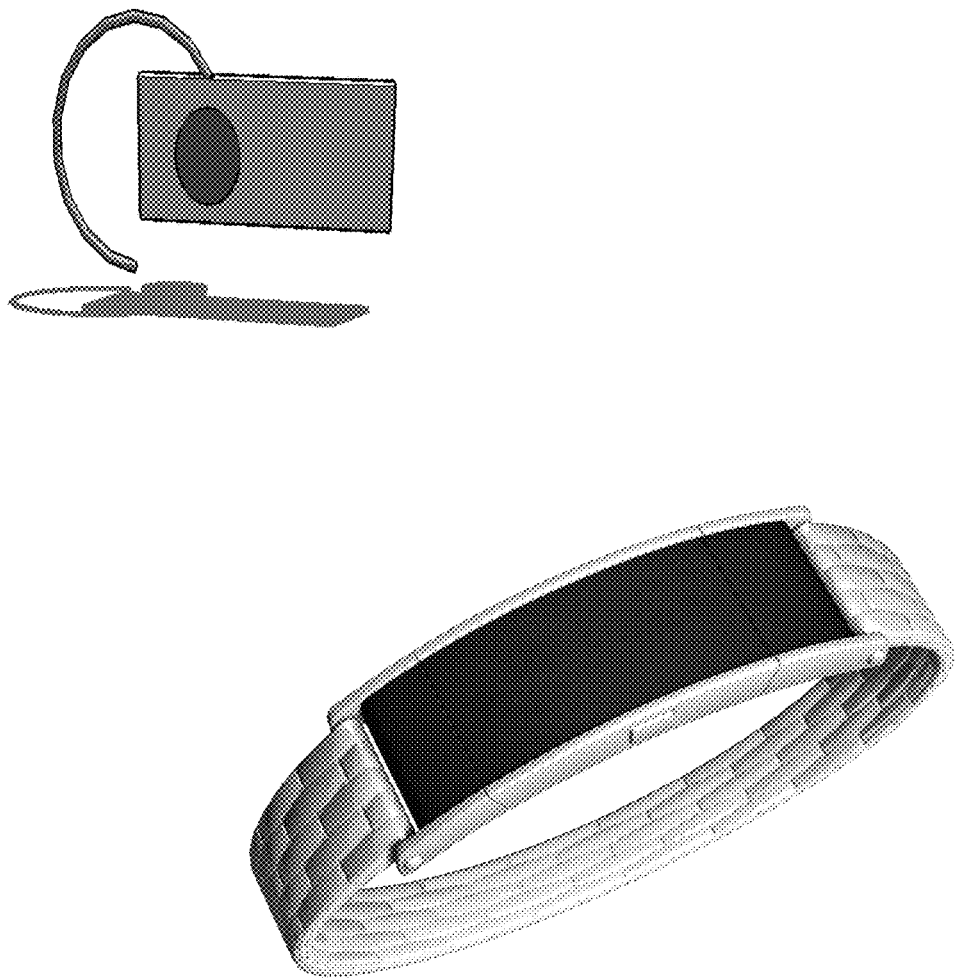

FIGS. 1A-1C are diagrams of embodiments of a wristband that includes the present invention. The wristband maybe a wristband including a display as shown in FIG. 1A. The display may be an LCD, e-Ink, one or more LEDs, or another type of user feedback/display system. The wristband includes one or more sensors, not shown.

FIG. 1B shows that the wristband may be incorporated into a watch, or similar mechanism. The watch may include the traditional components of a watch, in addition to sensors. The sensors may be in any part of the watch, including the watchband, watch face, etc.

FIG. 1C shows a wristband that does not have visual output mechanisms. The wristband is shown with a Bluetooth headset, which may be used to provide user interface capabilities (e.g. visual or aural feedback and/or input). This reduces the power consumption of the wristband, as well as the size. In one embodiment, the wristband only turns on the Bluetooth system when sending user messages, to preserve battery power.

The wristbands shown in FIGS. 1A-1C are merely exemplary embodiments, and different formats may be implemented. The wristband, in one embodiment, includes a communications system that enables it to be connected to a computer system, such as a mobile device, a laptop or desktop, or a remote server via a network. The connection may be a wired connection, such as a USB (universal serial bus), mini-USB, micro-USB, or audio connection, or a wireless connection such as Bluetooth, local area network-based connection, Wi-Fi, cellular network based connection, etc.

Although the device is referred to as a wristband, one of skill in the art would understand that a body-worn device worn on a different part of the anatomy (arm band, leg band, torso band, headband) or a body-worn device integrated into another worn device (eyeglass integrated, clothing integrated) may be utilized to provide these features. However, for simplicity, the term wristband will be used throughout this Specification, which should not be taken to restrict the locations that the device may be worn.

Figure 2:
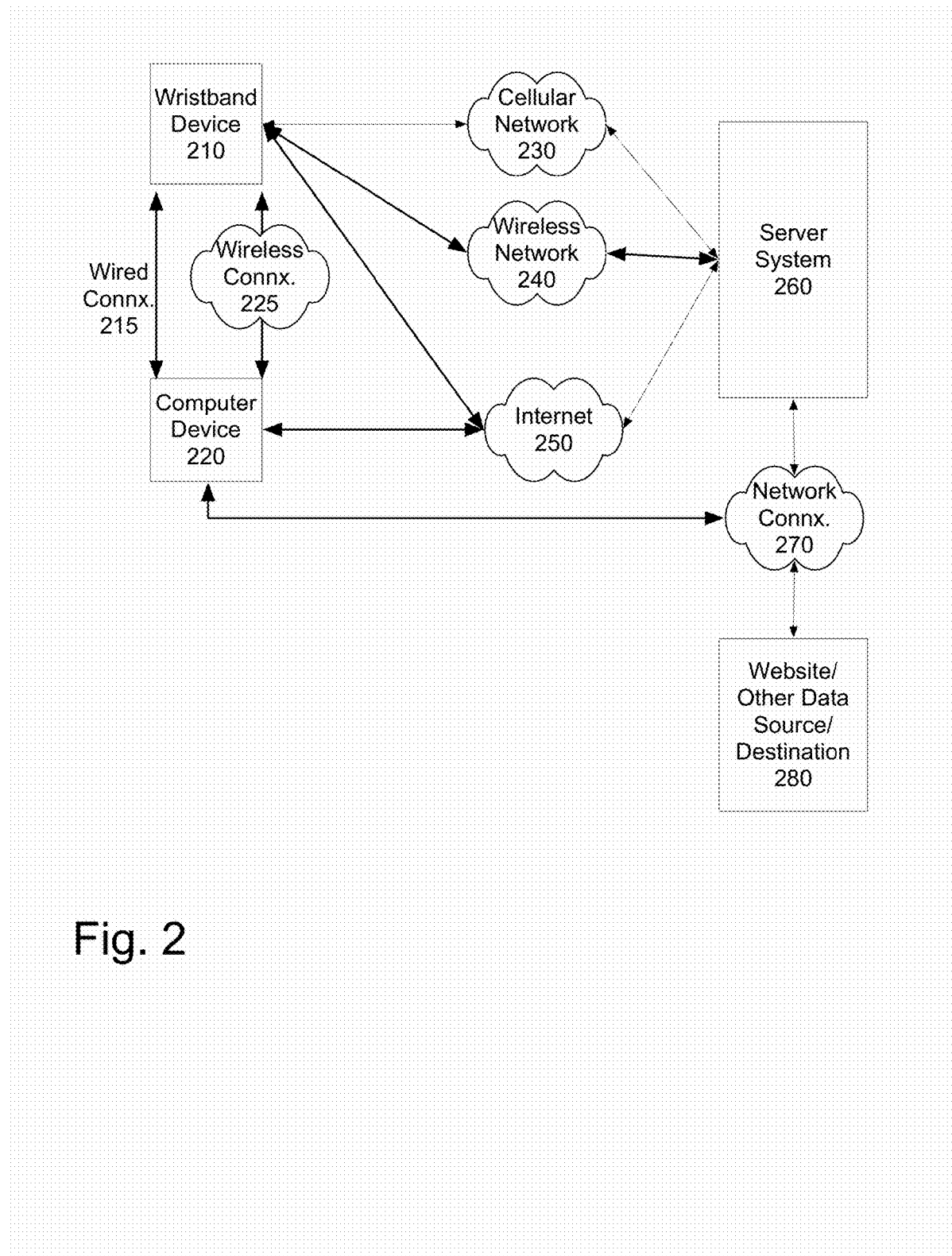
FIG. 2 is a block diagram of one embodiment of the system.

FIG. 2 is a block diagram of one embodiment of the system. The system includes the wristband device 210 which may be coupled to other devices via one or more of wired connection 215, cellular network 230, wireless network 240, and Internet connection 250. The wired connection 215 may be used to couple the wristband device to a computer device 220. The wired connection may be a TRS connector, such as an audio jack or audio plug, a USB connector (standard, mini, micro, USB3, etc.), or another type of connector whether male or female, integrated into the wristband device 210.

The computer device 220 may be a laptop or desktop computer, or a mobile device such as a smart phone. The computer device 220 may be used to provide additional user interface features. In one embodiment, the computer device 220 may also receive aggregate data collected by the wristband device 210. In one embodiment, certain calculations that are more processor-intensive take place on the computer device 220, or server system 260. This allows the use of a lower power processor on wristband device 210, leading to power savings.

The wristband device 210 may also be coupled to a server system 260 either directly through a network connection 230, 240, 250, or through computer device 220, to which the wristband device 210 is coupled. In one embodiment, the wristband device 210 is coupled to computer device 220 via a wired connection 215. Of course, the wristband device 210 may also be coupled to computer device 220 via a wireless connection 225. For example, the wristband device 210 may couple to computer device 220 through a Bluetooth or other local area network connection, a WiFi network, or another type of wireless connection 225.

Server system 260 may be used to provide default values, user interface features, calculations, and other features to wristband 210. In one embodiment, server system 260 may connect to websites, other data sources, and destinations 280 via a network connection 270. In one embodiment, server system 260 may also provide data to the user via another interface, such as a webpage.

In one embodiment, a local computer device 220 may replace the functionality of server system 260 described above, and server system 260 may be absent. Note that while individual devices are shown in this figure, the server may be a distributed system, with distributed database and other storage, distributed processing, etc. Such features are well known in the art for providing server system access.

Figure 3:
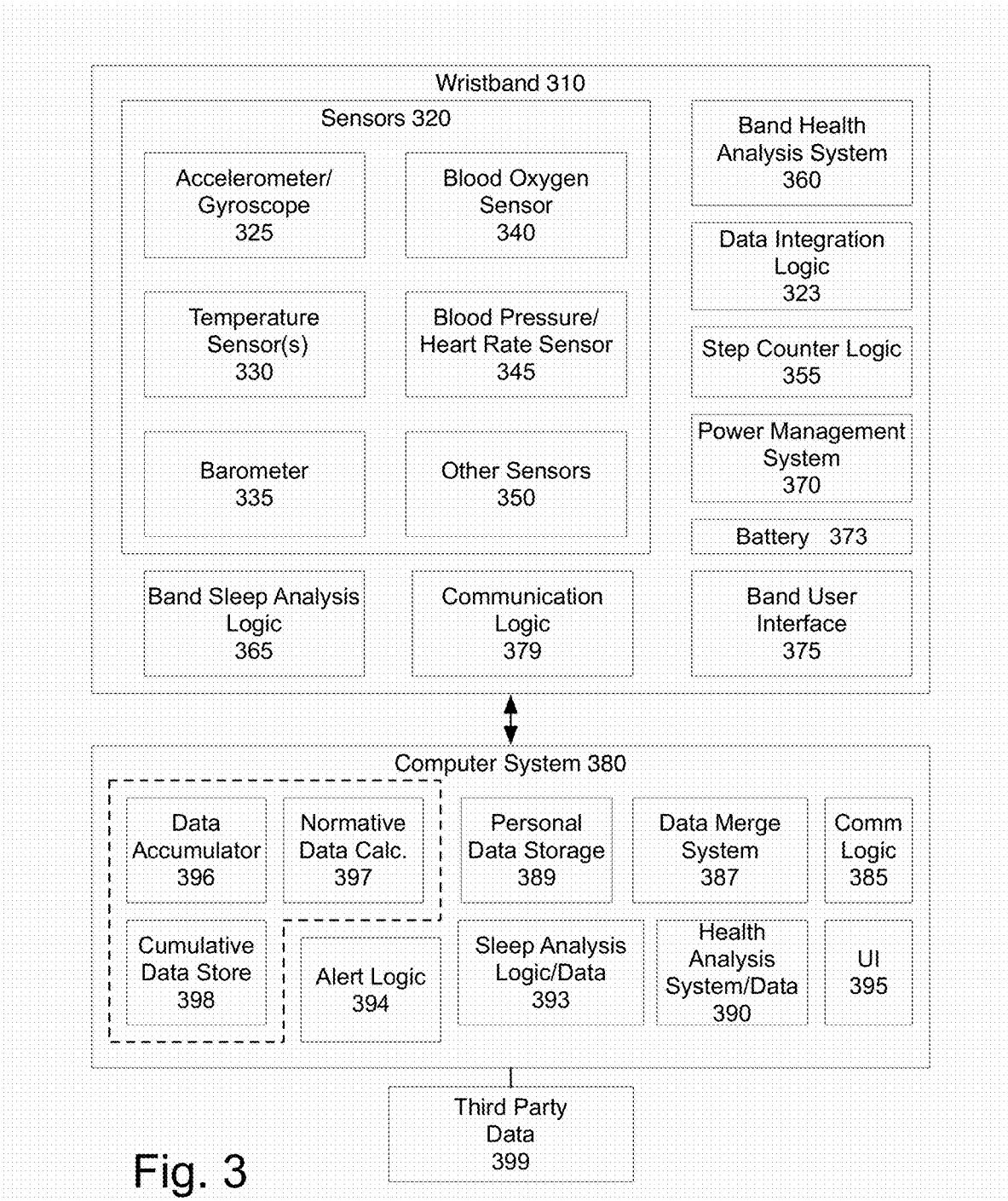
FIG. 3 is a block diagram of one embodiment of the wristband.

FIG. 3 is a block diagram of one embodiment of the wristband and a computer system. The computer system may be a local system, a server system, or a combination of a local system and server system.

The wristband 310 includes a plurality of sensors 320. The sensors 320 may include one or more of an accelerometer/gyroscope 325, thermometer(s) 330, barometer 335, blood pressure/heart rate sensor 345, blood oxygen sensor 340, pH sensor to determine acidity/alkalinity of the user's body, and other sensors 350.

In one embodiment, one or more thermometers 330 may be included as sensors 320. A single thermometer may be a body-facing thermometer (e.g. a thermometer designed to be in contact with the user's body to measure body temperature). A second thermometer 330, optionally, may be an ambient thermometer, e.g. a thermometer designed to not be in contact with the user's body, to measure ambient temperature. In a watch-like configuration, such thermometers may be located on the inside of the strap, and the face of the watch, respectively. In one embodiment, additional sensors, such as the blood pressure/heart rate sensor 345, blood oxygen sensor 340, and pH level sensor would also be designed to be in contact (either constantly or periodically) with the user's body. In one embodiment, a combination of sensors may provide additional data. For example, a combination of temperature changes and pH level changes, as correlated to activity level, may provide useful health data, not only as to the user's athletic conditioning and electrolyte levels but also an indication of the functioning of the glucose system of the user.

In one embodiment, the data from sensors 320 are sent to data integration logic 323. Data integration logic 323 maintains the integrated sensor data, including current and historical sensor data, and additional available data about the user, such as user profile, user medical conditions, etc.

In one embodiment, health analysis system 360 accesses the data through data integration logic 323. Health analysis system 360 uses data from sensors 320 to evaluate the user's health. In one embodiment, the process uses a combination of data to determine if the user is experiencing health problems. In one embodiment, for example, an elevated body temperature may be an indication of illness. In one embodiment, the process described in co-pending and co-owned U.S. patent application Ser. No. 11/740,884, entitled "Method And Apparatus For A Health Phone" is used to make this determination. In one embodiment, the health analysis system 360, receives data from computer system 380, which performs the more complex calculations.

In one embodiment, health analysis system 360 is designed to assist users with chronic conditions, such as Type 2 diabetes or high blood pressure. In one embodiment, the health analysis system utilizes an expert system that analyzes the user's behavior based on the sensor data. In one embodiment, the user's behavior may include activity level, eating, sleeping, and other data that may be obtained by the system. In one embodiment, additional external sensor data may be integrated. For example, the external sensor data may include blood sugar monitoring data. In one embodiment, blood sugar monitors may be included in the device as well.

In one embodiment, the health analysis system then provides recommendations to the user, based on the results of that analysis. In one embodiment, the expert system provide recommendations via the mobile device, an accessible website, email, or other communications method(s). For example, recommendations may be recommendation on how the user should move, when the user should move, when the user should eat, and what the user should eat. Other recommendations that can be derived by the expert system based on the available data may also be provided.

For example, for a Type 2 diabetic, the recommendation may be as broad as "you are sitting too much after you eat," or as specific as "you should go on a 16 minute walk at a pace between 60 and 90-steps per minute." In one embodiment, the health analysis system 360 may further integrate these recommendations with the medicines the user may be taking. For example, the health analysis system may indicate that if you follow the set recommendations, the amount of drugs taken could be reduced.

In one embodiment, the combination of acidity, core temperature, and heart rate data can be used by health analysis system 360 to determine a user's reaction to food, without receiving direct input regarding food intake. This can be useful, for example, in monitoring the user's glucose reactions without either measuring insulin or providing the carbohydrate content of food. In one embodiment, the user may indicate the start of a meal using a user interface 375, to ensure that the appropriate sensors 320 monitor the user's reactions to the meal. In one embodiment, excess carbohydrate consumption can be found in the increase in skin acidity, and change in core body temperature. This may lead the band 310 to provide feedback using user interface 375. The feedback may include recommendations for activity, or for altering eating patterns, or for the use of medications or preventatives.

In one embodiment, health analysis system may further utilize the user's temperature data and sleep pattern data to determine a woman's ovulation cycle. Ovulation is correlated with morning temperature variations in women. Therefore, by tracking the woman's body temperature throughout the day, band health analysis system 360 can provide fertility awareness. Fertility awareness is useful for conceiving, avoiding conception, and monitoring gynecological health. The analysis, in one embodiment, is based on long-term analysis of temperature data over multiple months. In one embodiment, this occurs on the computer system 380, rather than on the band 310.

In one embodiment, the system further includes step counter logic 355. Step counter logic 355, in one embodiment, uses data from accelerometer/gyroscope 325, and optionally other sensors, to count repetitive motions, such as steps. In one embodiment, other types of motions—e.g. bicycle pedal pumps, step climbing, etc.—may also be counted. In one embodiment, by combining the temperature data with the movement data, step counter logic 355 can additionally determine the intensity of a workout. When the ambient temperature is higher, or humidity is higher, a workout is higher intensity, even if the same steps are taken at the same time. When the user's body temperature rises, it is also an indication of a more intense workout. In one embodiment, step counter logic 355 can integrated data from sensors 320, to determine.

Power management system 370 in one embodiment uses the data from sensors 320 to manage power within wristband 310. In one embodiment, wristband 310 may include a low power processor and a higher power processor. In one embodiment, wristband 310 may include low power sensors and higher power sensors. For example, a temperature sensor is a relatively low power sensor, compared to a heart rate sensor or blood oxygen sensor. Power management system 370 determines when to activate and inactivate various sensors 320, or calculation systems, such as step counter 355, health analysis system 360, communication logic 379, and user interface 375. In one embodiment, power management system 370 controls which portions of the wristband 310 are active. In one embodiment, the power management system 370 may optimize the portions to be activated to maximize battery life. In one embodiment, wristband 310 includes a rechargeable battery 373. In one embodiment, power management system 370 has different settings based on the current battery level. For example, when the battery is low, the power management system 370 may disable certain sensors 320 that consume significant power.

In one embodiment, the sensor data may also be used by sleep analysis logic 365. Sleep analysis logic 365 uses the accelerometer data and temperature data, in one embodiment, to evaluate sleep quality, and time alarms. In one embodiment, band sleep analysis logic 365 may interface with computer system 380. In one embodiment, band sleep analysis logic 365 may use communication logic 379 to send signals to adjust local conditions to improve the user's sleep quality. In one embodiment, such local conditions may include local temperature, airflow, noise cancelation, white noise generation, and other conditions which may be influenced by one or more systems that optionally may be part or, or controlled by, the wristband.

User interface 375 may be part of the system. User interface 375 may include input and/or output mechanisms that enable the wristband to interact with the user. In one embodiment, user interface may simply be one or more LEDs. The system may alternatively, or additionally, include more complex user interface features, ranging from LCD/OLED/eInk or other types of screens to voice input/speaker output controls, or other input/output mechanisms. The user interface 375 may be used by Band Health Analysis system 360 to provide feedback, reminders, alerts, or other communication to the user. Step counter logic 355, and other logics may provide output through user interface 375.

Communication logic 379 communicates between the wristband and external systems. In one embodiment, communication logic 379 communicates between the wristband and a computer system 380. As noted above, in one embodiment, communication logic 379 may also communicate with a Bluetooth headset. Communication logic 379 may also communicate with other external devices, such as wireless capable thermostats or other environmental controls, as described above. Communication logic 379 may include multiple communication mechanisms, e.g. a micro-USB plug or port, a Bluetooth connection, a cellular network connection, and/or a WiFi connection. Other connection mechanisms may be used as well.

The wristband 310, in one embodiment, is designed to be coupled to a computer system 380. The computer system 380 may provide additional user interface features, through interface 395. This may include providing cumulative user data through a web-based interface, recommendations for the user through the web-based interface, the ability to securely share data, and other features. In one embodiment, the user interface 395 also may provide more complex outputs, for example, a user's steps taken over the day or week, comparison or statistics of activity and/or health data, etc. In one embodiment, the computer system 380 may also provide number crunching, such as analysis used by health analysis system 360, to reduce the processor load on the wristband.

In one embodiment, the data received by the computer system 380 through communication logic 385 is integrated into a data storage 389, which stores the user's cumulative data. In one embodiment, data merge system 387 enables the merging of data from multiple devices, such as multiple wristbands, mobile devices, external sensors, user input, medical records, and/or other data sources for user information.

Health analysis system/data 390 may process health data gathered by sensors 320 in the wristband 310. In one embodiment, health analysis system 390 works with health analysis system 360 to process data and provide appropriate feedback to the user. In one embodiment, health analysis system/data 390 may also have initial settings, which indicate "normal" conditions for the user based on initial user information. Health analysis system/data 390 may also adjust the initial conditions information, based on collected statistical data. In one embodiment, health analysis system/data 390 may provide recommendations, alerts, and/or warnings to the counterpart application in the wristband.

In one embodiment, sleep analysis logic/data 393 may use data from band sleep analysis logic 365, and may provide processing of sleep information. In one embodiment, sleep analysis logic/data 393 may also be used to set initial sleep conditions, based on user information. Sleep analysis logic/data 393 may also adjust the initial conditions information, based on collected statistical data.

Computer system 380 may be a server, which receives data from many users. In one embodiment, a normative settings, e.g. the values for a "normal person with the following parameters" is determined based on data collected from a large number of users. In one embodiment, data accumulator 396 collects data from data merge systems 387 and/or data integration logics 323. In one embodiment, the data collected includes attached metadata which indicates the user's additional profile information, e.g. age, gender, medical conditions, etc. In one embodiment, the data collected is anonymized.

Normative data calculator 397 in one embodiment utilizes the data from data accumulator 396 to calculate the interrelated measurements for users, and the modifiers for various profile elements. For example, normative data calculator would calculate the normal person's sleep cycles, core body temperature during those sleep cycles, and other relevant measurements. The system would be capable of adjusting the "normal person's" data to account for a woman's cycle, a diabetic's different reactions, a chronic illness, etc.

Cumulative data store 398 in one embodiment stores the data calculated by normative data calculator 397. This data may be shared with computer systems 380 and bands 310. In one embodiment, alert logic 394 may use the normative data, as adjusted for the user, to send alerts when abnormal behavior's of the user's body systems are observed. For example, thyroid functioning, glucose reactions, sleep health, as well as other deviations from the normal pattern would be detectable and the user may be appropriately alerted. In one embodiment, any alert may be associated with a level of probability. For example, an alert may be "You have an elevated body temperature, we believe is the result of high blood glucose (60% probability)." The user may optionally receive the additional information, of other possible causes of the observed information. For example, if the user asks for more information, the system may provide further information such as "The temperature may alternatively be the result of infection (25%) or flu (15%)." In this way, the results of the integrated data from multiple sensors are used to provide useful guidance and information to the user. In one embodiment, the user's integrated data also becomes of the cumulative data store, setting the normative data.

In one embodiment, computer system 380 may be coupled to other systems, to obtain third party data 399.

Third party data may include medical data associated with the user, new studies that may impact the health analysis system or power management system, data from other users' systems to enable social media, etc. In one embodiment, the computer system 380 may also send data to third parties, packaged as third party data 399. This data may be aggregate data from a plurality of users, an individual user's data. The data may be sent to a social media site, friends, and/or medical professionals. In one embodiment, the data sharing, and data collected, may be set up by user when the user configures the wristband 310. In one embodiment, such configuration is done through the user interface 395 of a computer system, since that provides a better interface than the wristband 310.

Figure 4:
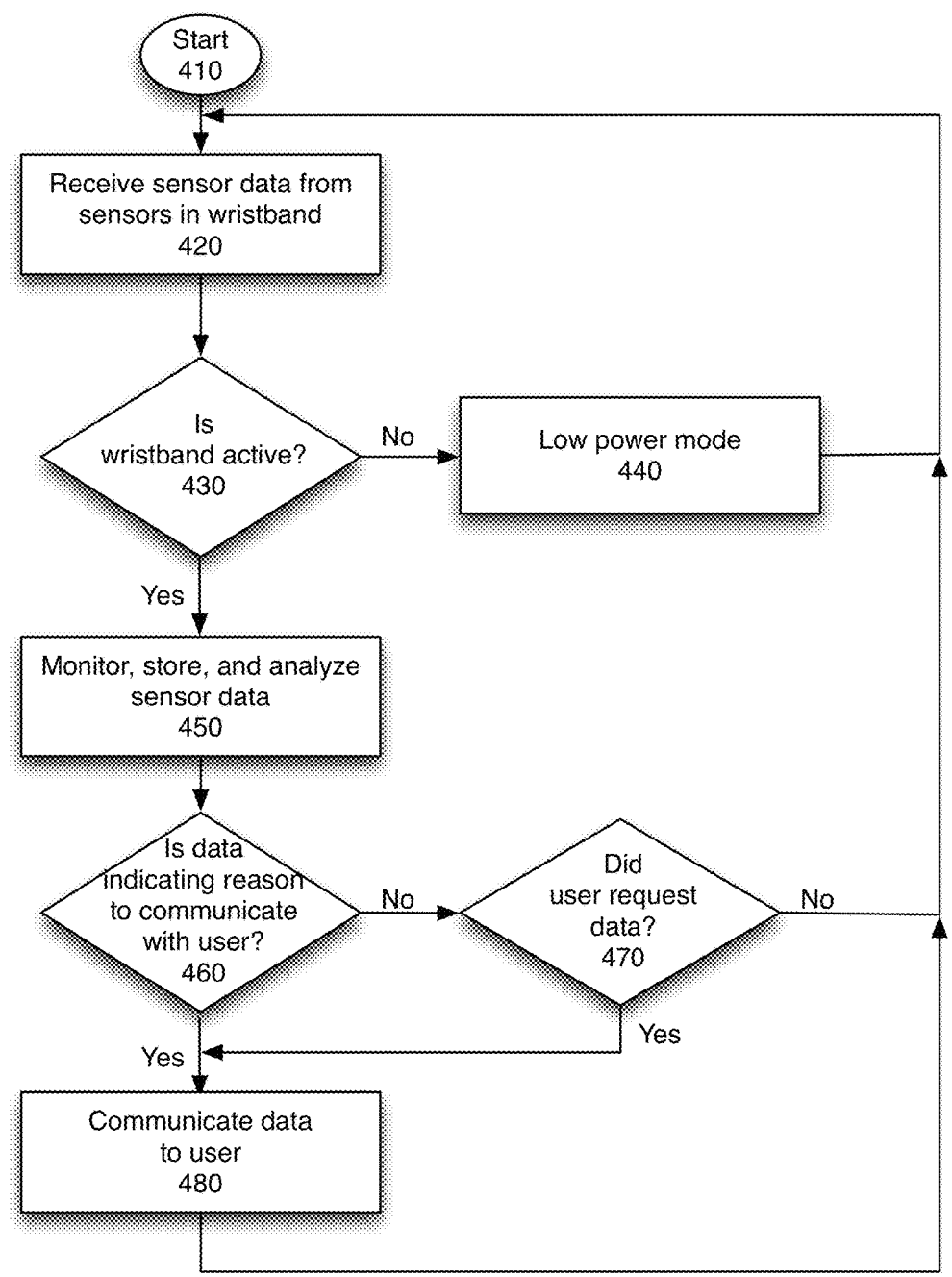
FIG. 4 is a flowchart of one embodiment of using the wristband sensors.

FIG. 4 is a flowchart of one embodiment of using the wristband sensors. The process starts at block 410. In one embodiment, this process runs whenever one or more sensors are powered. At block 420, sensor data is received from one or more sensors. In one embodiment, each sensor has an associated frequency of update. For example, an accelerometer may obtain accelerometer data every 0.25 seconds, while a thermometer may measure the temperature every minute, and a heart rate monitor may be turned on to get a heart rate every five minutes.

In one embodiment, the frequency is adjusted based on the current use of the wristband. In one embodiment, the frequency is adjusted based on the current use of the wristband, in combination with a battery level available. One embodiment of adjusting the accelerometer testing frequency is described in U.S. patent application Ser. No. 12/472,361, entitled "Method And Apparatus For A Motion State Aware Device." Other sensors are be adjusted similarly, in one embodiment, with differences based on the nature of the sensor. For example, body temperature needs to be sampled much less frequently than an accelerometer that is monitoring human motion. A temperature sensor that is monitoring ambient temperature needs to be monitored even less frequently than a temperature sensor monitoring body temperature. A heart rate monitor observing a steady heart rate may be turned on every five minutes, but if an unusual heart rate is measured, the heart rate monitor may be turned on more frequently to ensure that an accurate representation of the heart rate is captured.

At block 430, the process determines whether the wristband is active. In one embodiment, the wristband is active when the user is wearing the wristband and inactive when the wristband is not being worn. In one embodiment, sensor data is used to determine whether the wristband is being worn. In one embodiment, temperature data, accelerometer data, and other sensor data, alone or in combination, may be used to determine whether the wristband is being worn. Since the wristband is measuring user health data primarily, it is considered inactive when not worn. If the wristband is inactive, at block 440 it is put into low power mode. Low power mode, in one embodiment, reduces the sensor testing frequencies, and may put portions of the wristband to sleep, or turn them off. The process then loops back to block 420, to await new sensor data.

If the wristband is found to be active, at block 450, the sensor data is monitored, stored, and analyzed. In one embodiment, the data that is analyzed is cumulative data (e.g. data based on a set of collected sensor data from a particular sensor.)

At block 460, the process determines whether the data indicates a reason to communicate with the user. If so, at block 480 data is communicated to the user. This may be done through a user interface output or by pushing output to another device (e.g. a mobile device, computer system, web page or other output via Bluetooth, email, WiFi, SMS, etc.). The process then returns to block 420 to await further sensor data.

If the data does not indicate a need to communicate, the process continues to block 470. At block 470, the process determines whether the user has requested data. For example, the user may request a reminder every hour of how many steps he/she has taken today. Thus, data requests may be immediate (e.g. tap on wristband to obtain current step count), or prospective (report lack of user motion after one hour, reminder user to stretch for 5 minutes, etc.) If there is a user request for data, the process communicates with the user at block 480. In one embodiment, the same methods of communication, e.g. directly, through a computer system, through a mobile device, via web page, or other interface, may be used. The process then returns to block 420. If the user did not request data, the process directly returns to block 420. In this way, the wristband uses the sensor data to monitor, and provide information to the user.

Figure 5:
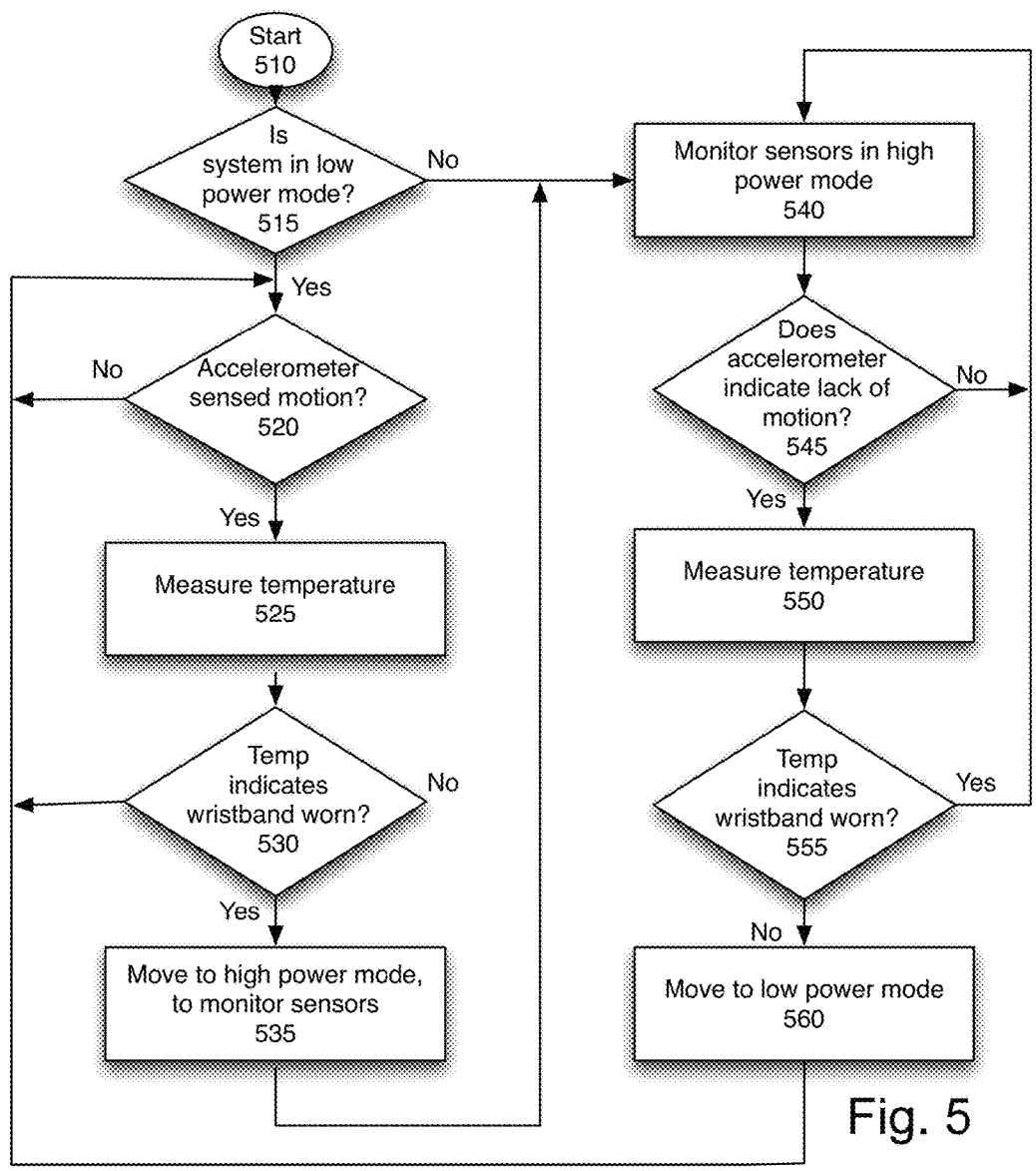
FIG. 5 is a flowchart of one embodiment of using sensors in the wristband to determine set power mode.

FIG. 5 is a flowchart of one embodiment of using sensors and motion sensors in the wristband to set power mode. This is an exemplary use of one of the sensors in the wristband. It would be understood by one of skill in the art that similar use may be made of other sensors. In one embodiment, the temperature sensor is selected for this process because it is a low power sensor, relatively speaking. The process starts at block 510. In one embodiment, this process is initiated when the wristband is turned on.

At block 515, the process determines whether the system is in low power mode. If it in low power mode, the process at block 520 determines whether the accelerometer has detected motion. If not, the process continues to monitor the accelerometer. Note that when the system is in low power mode, in one embodiment, the accelerometer read frequency is lower than in active mode.

If the accelerometer sensed motion, at block 520, the temperature is measured, at block 525. At block 530, the process determines whether the temperature indicates that the wristband is being worn. In one embodiment, this determination uses the body-contact thermometer and the ambient thermometer. In one embodiment, the process first uses the body contact thermometer only, and if the body contact thermometer indicates that the temperature is in the correct range (generally 96 to 104 degrees Fahrenheit), then it determines a delta or differential between the body contact thermometer and the ambient temperature thermometer, to ensure that the temperature is not the result of the wristband being in a warm environment, but not worn by the user.

If the temperature indicates that the wristband is being worn, at block 535, the wristband is moved to the high power mode, to monitor the sensors. In one embodiment, the determination of the periods of time that the wristband is being worn is logged with the other health data. This data is used when integrating the sensor data, as will be described in more detail below.

If the temperature does not indicate that the wristband is being worn, e.g., the body contact thermometer's reading is out of range or identical to the ambient temperature thermometer, the process returns to block 520 to continue monitoring for accelerations. In one embodiment, if a number of accelerations are identified in a row, with the thermometer indicating that the wristband is not worn, the process may move to high power mode at block 535, under the assumption that the thermometer is broken, or the user is wearing the wristband incorrectly, not in contact with the user's body, e.g. over a sleeve. In one embodiment, in this case, a notification may be sent to the user, enabling the user to correct the problem with the thermometer, indicate that the wristband is not being worn, and/or take the wristband for repairs.

At block 540, the sensors are monitored in a high power mode.

At block 545, the process determines whether the accelerometer indicates a lack of motion. If it does not, the process continues to monitor the sensors in high power mode. In one embodiment, while the system is designated as being in a "high power" mode this does not indicate that all sensors are being continuously monitored. Rather, this simply indicates that the frequency of sensor readings for at least one of the sensors is at the "active wristband" level.

If the accelerometer indicates a lack of motion, at block 550, the temperature is measured.

At block 555, the process determines whether the temperature indicates that the wristband is being worn. In one embodiment, this determination uses the body-contact thermometer and the ambient thermometer. In one embodiment, the process first uses the body contact thermometer only, and if the body contact thermometer indicates that the temperature is in the correct range (generally 96 to 104 degrees Fahrenheit), then it determines a delta between the body contact thermometer and the ambient temperature thermometer, to ensure that the temperature is not the result of the wristband being in a warm environment, but not worn by the user.

If the temperature indicates that the wristband is being worn, the process returns to block 540. If the temperature indicates that the wristband is no longer being worn, the process at block 560 moves the wristband to a low power mode. The process then continues to block 520, to continue monitoring the wristband in low power mode.

As in the movement to the active mode, in one embodiment, a temperature sensor error can be overridden if the consistent data from accelerometer, or other sensors, shows that the wristband is being worn. In one embodiment, the system is more likely to move to the active mode with the error assumption than the inactive mode. This is because the only effect of over-monitoring is reduced battery life, while the effect of under-monitoring is failure to accurately capture user activity data.

Figure 6:
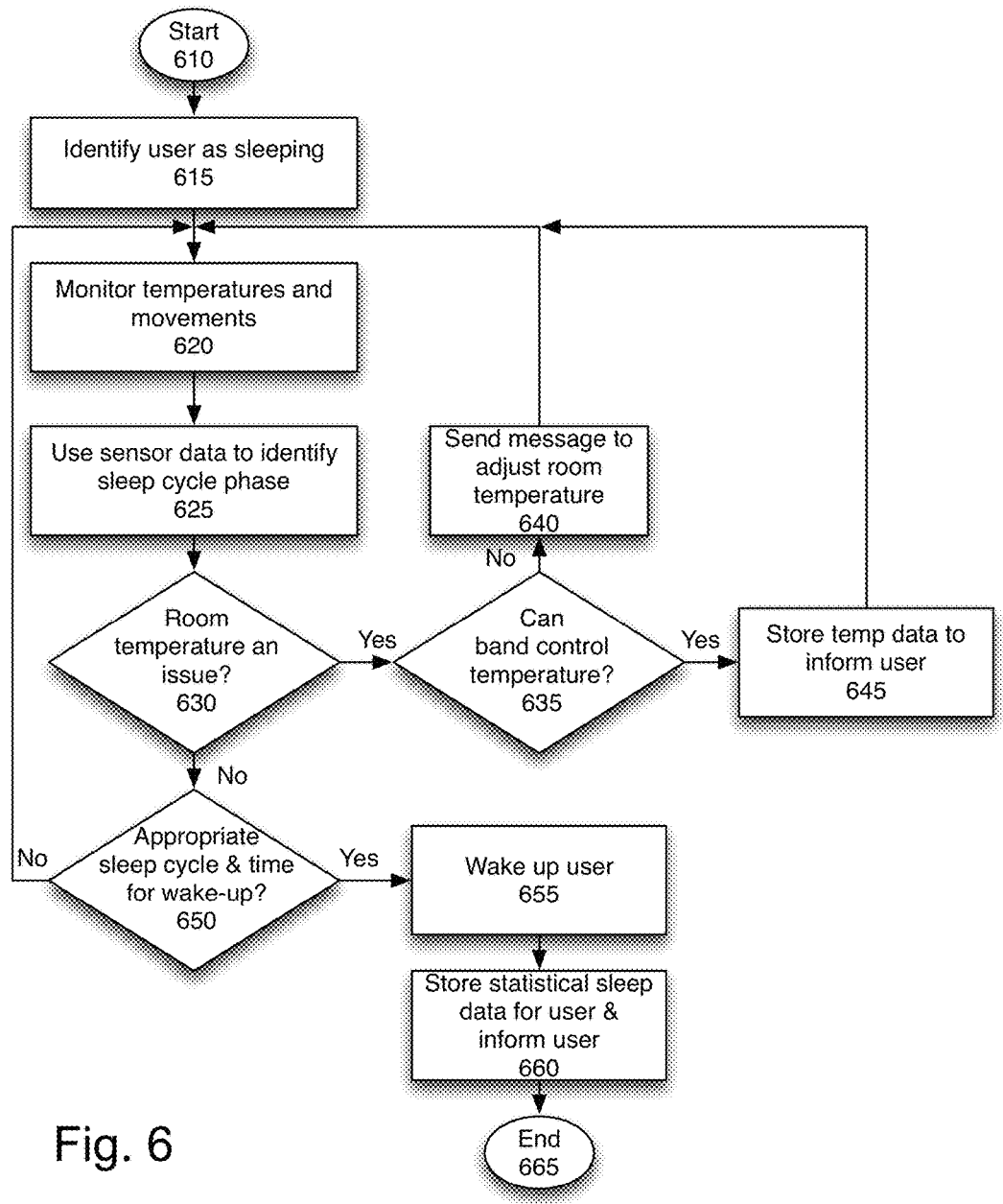
FIG. 6 is a flowchart of one embodiment of using the wristband for sleep management.

FIG. 6 is a flowchart of one embodiment of using the sensor data, including temperature data, for sleep analysis. The process starts at block 610. At block 615, the user is identified as sleeping. In one embodiment, this may be done based on accelerometer data, time of day, statistical record of user sleep, user input, or any one or more of the above.

At block 620, the process monitors temperature data and movement data, e.g. data from an accelerometer, gyroscope, or other movement sensor. In one embodiment, the temperature data monitored includes the user's body temperature as well as the ambient temperature.

At block 625, the process identifies the user's sleep phase based on body temperature and/or accelerometer data. In one embodiment, the user's body temperature is used to determine the sleep cycle phase. The correlation between the changes in body temperature and the various sleep cycles improves accuracy in determining the sleep phase of the user, which enables more accuracy in waking the user up at the optimal time.

At block 630, the process determines whether the room temperature is an issue. Too high or too low ambient temperature can negatively impact sleep quality. This may be determined based on a combination of sleep quality measurements (based on body temperature, accelerometer, and sleep phase timing), and ambient temperature measurements. If the room temperature is an issue, the process continues to block 635.

At block 635, the process determines whether the band can control the local temperature. In one embodiment, if the thermostat is network-controlled, the wristband may be able to control the local ambient temperature. If that is the case, at block 640, the wristband sends out a signal, to adjust the local temperature. The process then returns to block 620, to continue monitoring temperatures and movements.

If the band cannot control the temperature, as determined at block 635, the process at block 645 stores the temperature data to inform the user of the room temperature problem. This enables the user to correct this problem, in future sleeping environments. The process then returns to block 620, to continue monitoring. In one embodiment, this logic, described from block 630 to 645, may be optionally excluded, or optionally turned off by the user.

If at block 630, the room temperature was not determined to be an issue, the process continues to block 650. At block 650, the process determines whether it is the appropriate time to wake up the user. In one embodiment, this is based on the sleep cycle determination, and the user's alarm settings. If it is not yet time to wake up the user, the process returns to block 620 to continue monitoring.

If it is time to wake up the user, at block 655, the user is woken up. In one embodiment, the statistical sleep data is then stored for the user, at block 660. In one embodiment, at block 660, the user may be informed of room temperature issues, sleep length, sleep quality, etc. In one embodiment, the user may also be asked to provide data about the subjective sleep quality. The process then ends at block 665. The gathered statistical data may be used by health analysis system, sleep analysis system, and other aspects of the system to provide recommendations, adjust settings, or otherwise improve the user's future sleep quality and quality of life.

Figure 7:
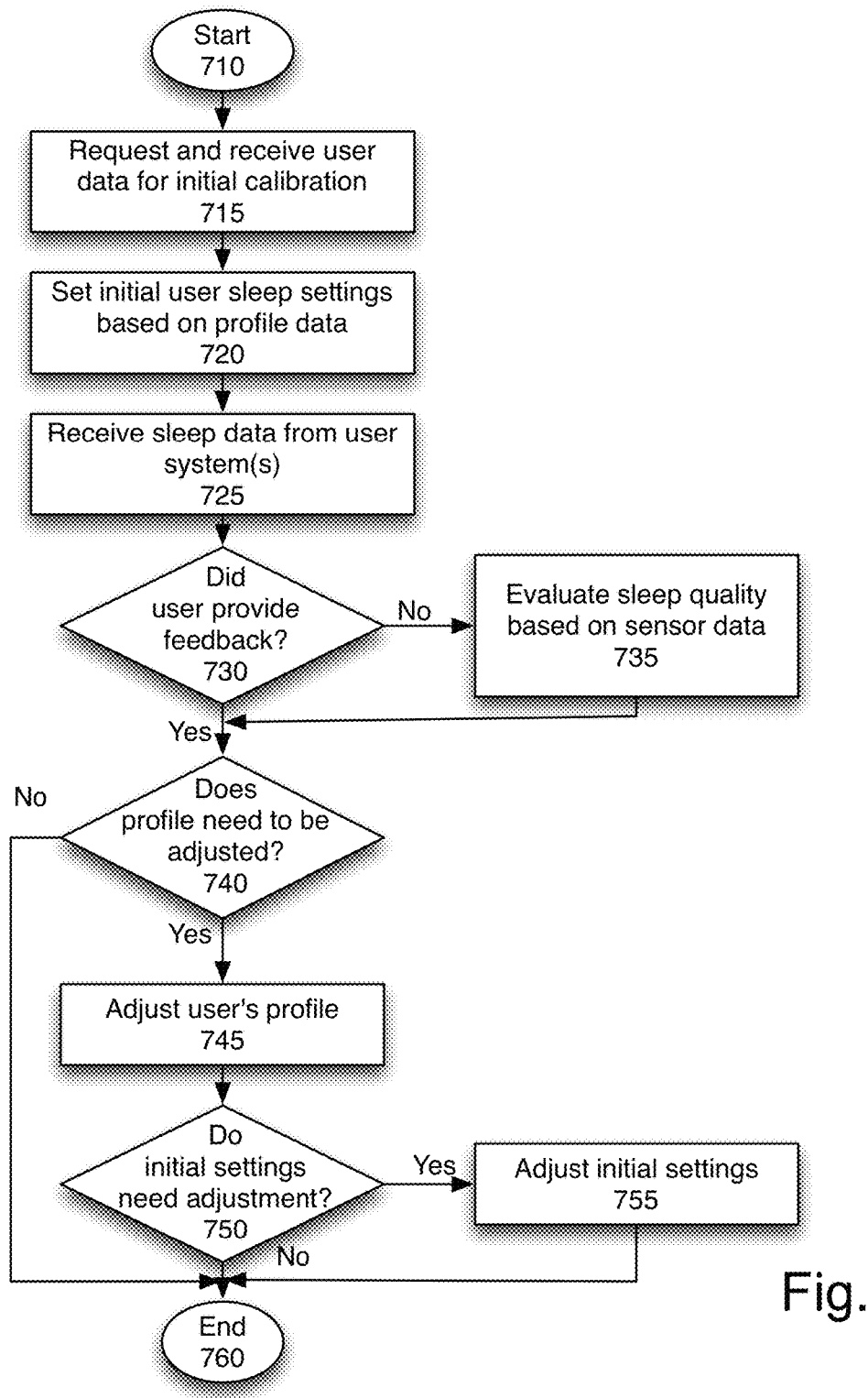
FIG. 7 is a flowchart of one embodiment of calibration for sleep management.

FIG. 7 is a flowchart of one embodiment of calibration for sleep determination. The process starts at block 710. In one embodiment, the process starts when the system is initially set up or the user initiates the calibration.

At block 715, the system requests that the user provide some relevant user profile data. In one embodiment, user profile data is collected. Calibrating the sleep monitoring logic to a given user based on their user profile results in more accurate sleep cycle determination, and thus more restful sleep and better waking time determination. A user's height, weight, age, and gender generally correlates with motion patterns during various phases of sleep. Therefore, the user profile data may be used for setting initial sleep cycle and accelerometer data evaluation.

At block 720, the user profile data is received, and the initial user sleep settings are set based on the user profile data. In one embodiment, the initial user sleep settings are based on studies, scientific research, and/or statistical data obtained by the system from users. This completes the initial set-up.

At block 725, sleep data is received from the user system(s). Sleep data may include time, sleep cycle data, ambient temperature and other environmental data, and optionally user feedback.

At block 730, the process determines whether the user provided feedback. In one embodiment, during an initial calibration period, the system asks the user one or more questions after each sleep session, such as how rested they feel and whether they were happy with the length of their sleep. In one embodiment, the user may further optionally provide feedback at any time.

If no user feedback was received, the process continues to block 735, where the sleep quality is evaluated based on the sensor data. The process then continues to block 740. At block 740, the process determines whether the user's sleep profile should be adjusted. The user sleep profile should be adjusted, if the profile does not match the user's actual sleep pattern, and leading to non-restful sleep.

If the sleep profile needs to be adjusted, the process continues to block 745, and adjusts the user's profile. The user's sleep profile determines the default length of each sleep cycle, in one embodiment.

At block 750, the process determines whether the initial settings need adjustment. The initial settings, based on the user profile data, may need to be adjusted, based on subsequent information. For example, it may be that initially, the system does not differentiate between users of different genders. However, if one gender's sleep profiles are consistently adjusted in the same way, the default initial settings may be adjusted correspondingly. In one embodiment, in order to adjust the initial settings, the aggregate data should reflect a statistically significant correlation between the change from the initial settings and a factor. If that is the case, at block 755, the initial settings are adjusted. The process then ends at block 760. In one embodiment, adjustments are reflected back to the default settings associated with individuals sharing the user's characteristics.

Figure 8:
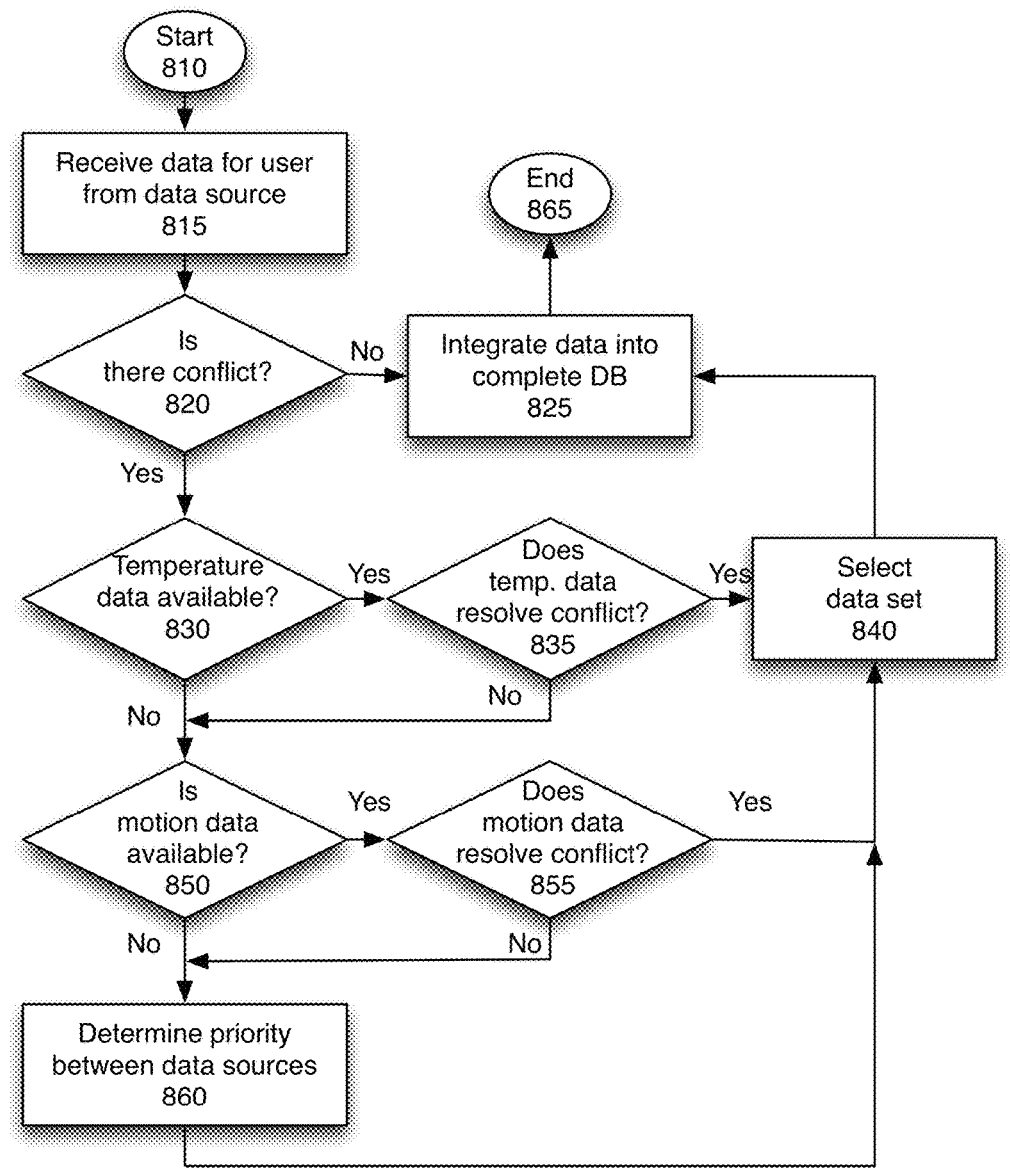
FIG. 8 is a flowchart of one embodiment of using the sensor data for data set merging.

FIG. 8 is a flowchart of one embodiment of merging data sets. In one embodiment, users may have multiple devices that collect sensor data, indicating user conditions of various types. As users have more and more devices tracking/monitoring them—headset, wristband, mobile phone, medical devices, sensors, and other wearable technology—users generally want to have a single data set that they can view and use to evaluate their health status, progress, and condition. The system also gains a better understanding of the user as more data is incorporated, and provides more accurate recommendations. Thus, it makes sense for many reasons to merge data together into one system. The process starts at block 810. In one embodiment, this process starts whenever new data is sent to a computer system.

At block 815, data is received for a user, from a data source. The data source may be the wristband described above, a medical device, a mobile device, or another type of data source. In one embodiment, this may be a non-sensor data source, such as a website or program which includes data from a different sensor, or information from the user's medical history or user input.

At block 820, the process determines whether there is conflict between the received data and existing data in the system. There is conflict when there is data from two or more sources, for the same period, with the same data type. In some cases, devices may track different variables/health-parameters. For example, device A may track activity and device B may track heart rate. These two data sets are not in conflict, when they overlap in time. Therefore, merging the data sets is simple, based on time information, associated with each data set.

If there is no conflict, at block 825, the data sets are merged. In one embodiment, the data sets are associated with an exact time, and placed in what is effectively a timeline of user data. Having such a merged data set opens the opportunity to use post-processing to obtain more accurate information, and learn more about what happened to the user. The process then ends at block 865.

If there is a conflict, as determined at block 820, the process continues to block 830. At block 830, the process determines whether temperature data is available for evaluation. In one embodiment, temperature data must be available from both sources of data, e.g. both wristbands, in order to make this evaluation. In another embodiment, temperature data from one data source may be sufficient.

If temperature data is available, the process continues to block 835. At block 835, the process determines whether the temperature data resolves the conflict. Temperature data may resolve the conflict if one data source indicates that the sensor was being worn by the user, while the other data set indicates that the sensor was not being worn. If the temperature data resolves the conflict, at block 840 the correct data set is selected. The process then continues to block 825, to integrate the selected data set into the database. In one embodiment, the incorrect data set is discarded. In one embodiment, the incorrect data set is saved, as a sample of data that was obtained when the wristband was not worn.

If the temperature data does not resolve the conflict, or no temperature data is available, the process continues to block 850.

At block 840, the process determines whether motion data is available. Motion data is accelerometer data that may be used to determine whether a user is moving, and which user is moving. One Embodiment, The Gait Analysis Described In U.S. Pat. No. 7,917,768, Entitled "System Control Via Characteristic Gait Signature" May be used to make this determination.

If motion data is available, at block 855, the process determines whether the motion data resolves the conflict. The motion data may resolve the conflict by indicating the motion is inconsistent with a human motion pattern, indicating that the device is not being worn. The motion data may alternatively resolve the conflict by indicating that the motion is being made by someone other than the user. For example, a user may allow a friend to borrow, or have a child take a wristband or other sensor system. Since gait information may be used to uniquely identify the user, it may be used to resolve the question of whether the sensor data is associated with the user.

If motion data resolves the conflict, at block 855, the process continues to block 840 to select the appropriate data set, and then to block 825, to integrate the selected dataset into the database. In one embodiment, the incorrect data set is discarded. In one embodiment, the incorrect data set is saved, as a sample of data that was obtained when the wristband was not worn. If the motion data does not resolve the conflict, or no motion data is available, the process continues to block 860.

At block 860, the priority is determined. In one embodiment, a hierarchical list of data source precedence is used to decide which data is used of multiple sets of conflicting data. In one embodiment, a default hierarchy is established each time a new potentially conflicting sensor is added. For example, in one embodiment, if a user first purchases a black wristband, this wristband has the highest priority. A subsequently purchased wristband would then be assigned second highest priority and so on. In one embodiment, priority may be adjusted automatically based on usage data. For example, if the user has a first purchased wrist band A, and a later purchased wristband B, but user more frequently wears wristband B, the system may prioritize wristband B over wristband A, despite the purchase order. In one embodiment, the user may at any time, change the priority hierarchy.

Once the priority hierarchy is determined, at block 840, the data set is selected, and at block 825, the data is integrated into the database. In one embodiment, the user may manually adjust the system's automatic selections. In one embodiment, the conflicting data that is determined to be the "bad" data is not discarded but rather saved. The user may, in one embodiment, have the option to correct an incorrect prioritization/integration.

Of course while the other features are described in a flowchart form, one of skill in the art would understand that the determinations made, and evaluations may not be in the same order as shown. For example, in one embodiment, the system preferentially selects priority based on a user entered priority, if that is not available based on accelerometer data, if that is not available based on temperature data, and if that is not available based on a default priority setting. Alternative methods of executing the process may be used, as is known in the art. Furthermore, certain steps may be skipped.

Figure 9:
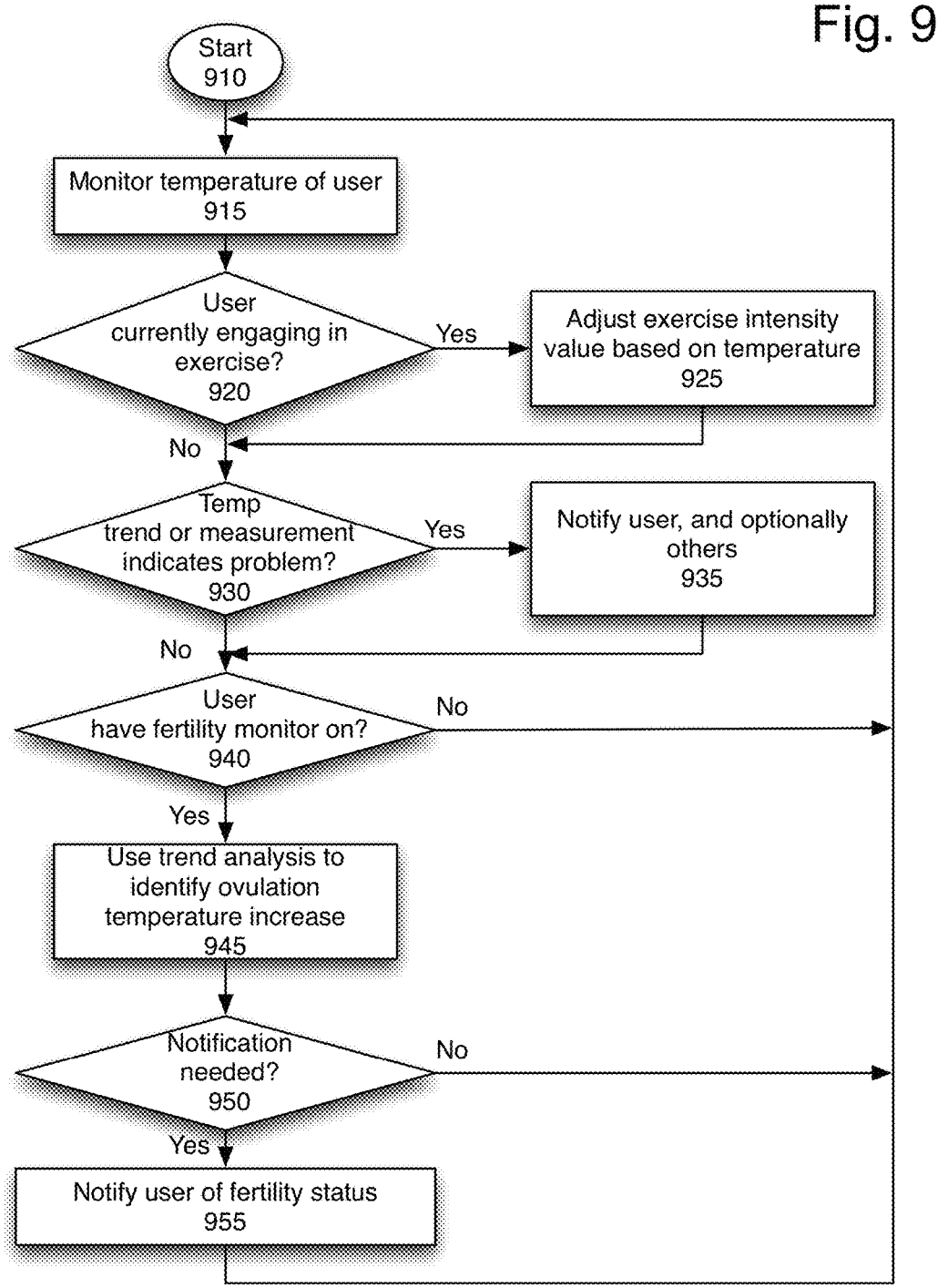
FIG. 9 is a flowchart of one embodiment of using the temperature sensors in the wristband.

FIG. 9 is a flowchart of one embodiment of using the temperature sensor on the band. In one embodiment, this process runs continuously when the band is being worn by a user. In one embodiment, this process starts at block 910, when the user puts on the band.

At block 915, the user's temperature is monitored. In one embodiment, the user's temperature is periodically tested by temperature sensor. In another embodiment, if the power use of the temperature sensor is low the monitoring may be continuous. In one embodiment, monitoring the temperature of the user includes monitoring a body temperature of a user and an ambient temperature, to separate the effects of ambient temperature on the readings.

At block 920, the process determines whether the user is currently engaging in exercise. If so, at block 925, the exercise intensity measurements are adjusted based on temperature. In one embodiment, in addition to tracking steps/movement, the system tracks exercise intensity, which is a function of movement and intensity, ambient temperature, and the user's body temperature. The process may continuously monitor the temperature during the user's workout. The process then continues to block 930.

If the user is not working out, the process continues to block 930. At block 930, the process determines whether the temperature trend and/or measurements indicates a potential health problem. Certain temperature patterns can indicate a health problem. The simplest example is that a fever is a problem. For example, low body temperature in the mornings has been associated with poor thyroid function. Other correlations, now known or later discovered, may be utilized to evaluate the long-term temperature data. If the temperature data, direct data or trending, indicates a problem, at block 935 certain actions are taken. In one embodiment, the user may be notified. In one embodiment, other parties, such as a doctor, may also or additionally be notified. In one embodiment, for certain conditions, the user may be provided with a recommended course of action. In one embodiment, system may further correlate additional sensor data with the temperature data, as is described in more detail below. The process then continues to block 940.

If the temperature measurement does not indicate a problem, the process continues directly to block 940.

At block 940, the process determines whether the user has the fertility monitor on. Optionally, a female user may monitor her fertility using the band. If the user is not monitoring, the process returns to block 915, to continue to monitor the user's temperature.

If the user is monitoring fertility, the process continues to block 945. At block 945, the system uses trend analysis to identify ovulation temperature increase. It is known that following ovulation, the user's body temperature can increase by 0.4 to 1.0 degrees. Because the user is most fertile in the two or three days before the temperature high point, using trend analysis over time enables the system to determine the entire fertility window, as well as identify the point of highest fertility.

At block 950, the process determines if the fertility determination needs to provide information to the user. If no notification needs to be provided, the process returns to block 915, to continue monitoring the user's temperature.

If information should be provided to the user, at block 955 the user is notified of her fertility state. The process then returns to block 915. In one embodiment, cumulative/statistical temperature data may be shared with a central database.

Figure 10:
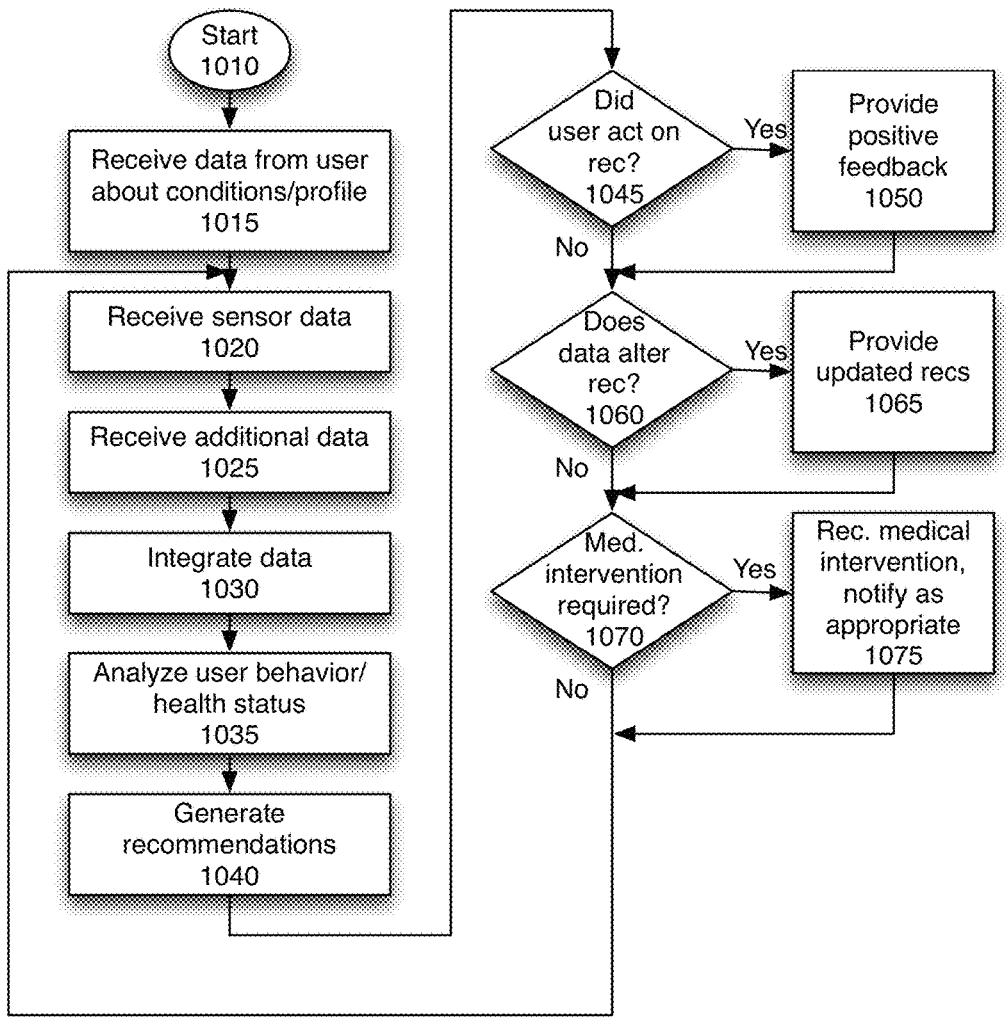
FIG. 10 is a flowchart of one embodiment of monitoring a medical condition using the wristband.

FIG. 10 is a flowchart of one embodiment of monitoring a medical condition using the wristband. The wristband includes one or more sensors, as noted above. In one embodiment, this process starts when the user initially sets up the band, and runs continuously when the band is worn and powered.

At block 1015, when the user initially interacts with the wristband, the user provides data about one or more conditions of the user. In one embodiment, a condition may be a chronic condition such as Type 2 diabetes, high blood pressure, respiratory diseases, etc. It is well known that close monitoring of a user with such conditions provides better health outcomes. The system, in one embodiment, uses the sensor data and other available in formation to provide an expert system based close monitoring, and relevant feedback. In one embodiment, the system may also provide notifications to the user as well as healthcare providers or other relevant data recipients.

At block 1020, the system receives sensor data from one or more sensors in the wristband.

At block 1025, the system receives additional data. In one embodiment, the additional data may be received from medical devices that can transmit their data or whose data can be entered by the user. For example, the medical device may be a blood glucose tester. In one embodiment, the tester may wirelessly transmit its results to the wristband or the associated computer system. In another embodiment, the user may manually add this information. In one embodiment, in addition to the user, medical professionals may optionally add data to the system. For example, if the user goes in and gets blood work done, the results of that blood work may be added into the system.

At block 1030, the data is integrated into a database, or other store of information about the user. In one embodiment, the data may include information from the user's profile, health conditions, sensor data, and additional data. In one embodiment, the data integration includes historical data (e.g. collected data over time) as well as current data.

At block 1035, the expert health analysis system utilizes the data to analyze user behavior and health status. In one embodiment, behavior and health status may include activity level, eating habits, medication need/use, sleep quality and quantity, etc.

At block 1040, the health analysis system generates and provides recommendations. In one embodiment, recommendations may include recommendations for movement, nutrition, environment, etc. Recommendations may include, how they move, when they move, where they move, and when and what to eat, etc. In one embodiment, the recommendation may be immediate, e.g. "you should take a 15 minute walk now," general "you should eat breakfast sooner after you get up," and/or aspirational "if you walked for 15 minutes after every meal, you would need to take fewer drugs for your condition.

At block 1045, the process determines whether the user accepted and acted on the recommendations. In one embodiment, if the user acts on the recommendations, at block 1050 the system provides positive feedback to encourage the user to continue following the recommendations.

At block 1060, the process determines whether any of the data would potentially alter the recommended treatment for the user. For example, if a diabetic patient starts walking regularly and having fasting blood sugars in the healthy range, the use of insulin may be reduced. Similarly, for a patient with a respiratory chronic illness, an increase in lung capacity, based on sustained running or other aerobic exercise, may reduce the need for inhalers or drugs.

If the user's activities potentially alter the recommended treatment, the system in one embodiment, at block 1065 alters the recommendations for the user. In one embodiment, the system also notifies the user to visit his or her healthcare provider to receive medical advice based on the difference between the predicted treatment based on the expert health analysis system and the user's current prescriptions.

At block 1070, the process determines whether any of the health indicators of the user, any of the sensor data, requires medical intervention. In one embodiment, for example, the insulin levels of an insulin-dependent diabetic may slip slowly over time. Because the system retains historical data, the use of the historical and current data would enable the expert health analysis system to recommend that the user visit a healthcare practitioner earlier. If the system recommends medical intervention, the user may be notified, at block 1075. Additionally in one embodiment, others may be notified as well. These others may be the user's family members, as set up in the system, the user's healthcare provider, etc. The process then returns to block 1020 to continue monitoring the user.

While this process was described as a flowchart, one of skill in the art would understand that in one embodiment, the system monitors, updates the analysis, determines recommendations, and provides recommendations on an as needed basis. The sequence of determinations need not occur as shown in this flowchart, or other flowcharts in this application. In one embodiment, the system continuously monitors the user's activity and sensor data information.

In one embodiment, although the user of the health analysis system was described with respect to a chronic condition, a temporary/acute condition may also be similarly monitored. For example, if a user is recovering from acute pancreatitis, or a broken leg, the monitoring may provide information and recommendations. In one embodiment, the healthcare provider may supply a wristband to the user, to provide close monitoring without requiring direct supervision of a user.

Figure 11:
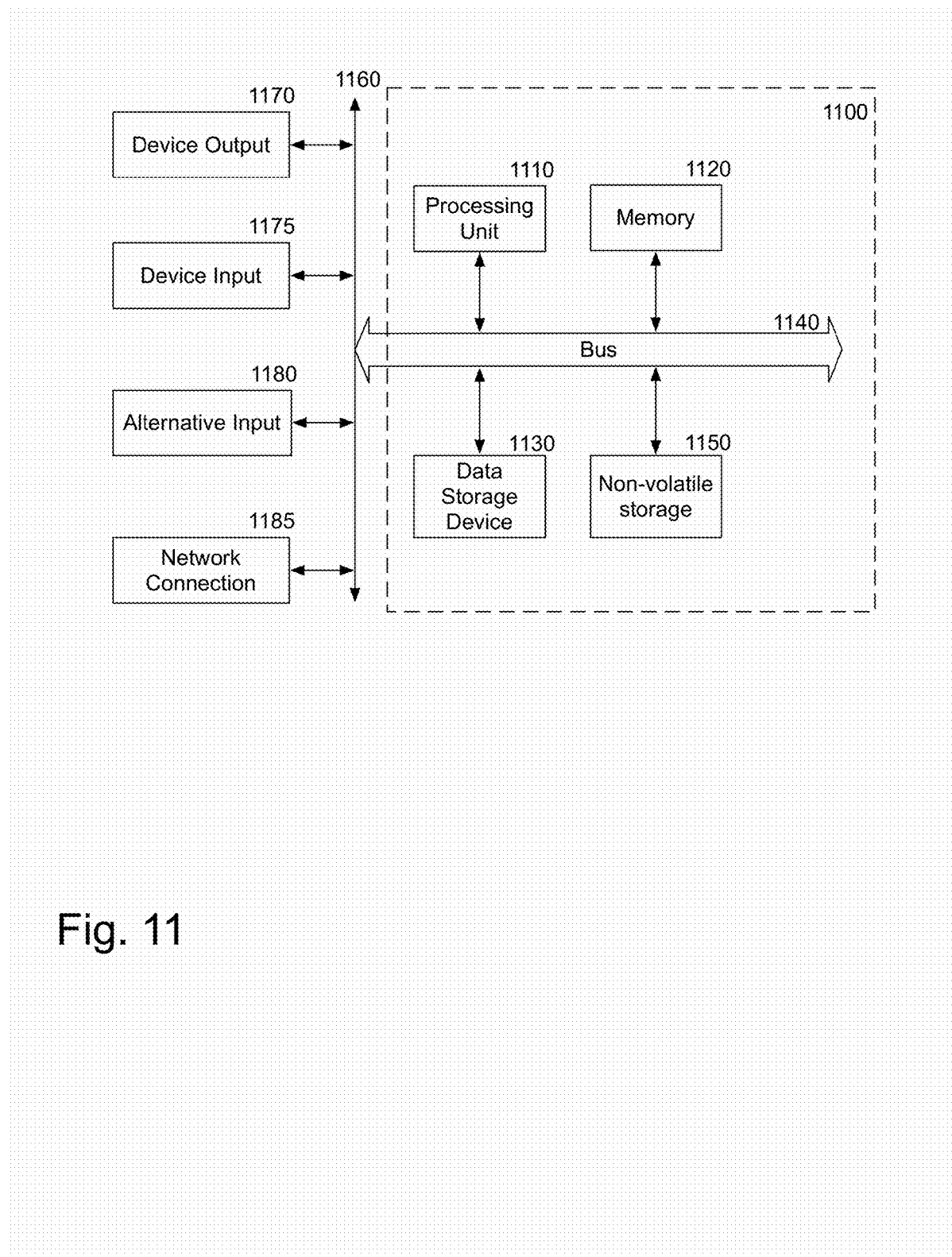
FIG. 11 is a block diagram of one embodiment of a computer system that may be used with the present invention.

FIG. 11 is a block diagram of a particular machine that may be used with the present invention. It will be apparent to those of ordinary skill in the art, however that other alternative systems of various system architectures may also be used.

The data processing system illustrated in FIG. 11 includes a bus or other internal communication means 1140 for communicating information, and a processing unit 1110 coupled to the bus 1140 for processing information. The processing unit 1110 may be a central processing unit (CPU), a digital signal processor (DSP), or another type of processing unit 1110.

The system further includes, in one embodiment, a random access memory (RAM) or other volatile storage device 1120 (referred to as memory), coupled to bus 1140 for storing information and instructions to be executed by processor 1110. Main memory 1120 may also be used for storing temporary variables or other intermediate information during execution of instructions by processing unit 1110.

The system also comprises in one embodiment a read only memory (ROM) 1150 and/or static storage device 1150 coupled to bus 1140 for storing static information and instructions for processor 1110. In one embodiment, the system also includes a data storage device 1130 such as a magnetic disk or optical disk and its corresponding disk drive, or Flash memory or other storage, which is capable of storing data when no power is supplied to the system. Data storage device 1130 in one embodiment is coupled to bus 1140 for storing information and instructions.

The system may further be coupled to an output device 1170, such as a cathode ray tube (CRT) or a liquid crystal display (LCD) coupled to bus 1140 through bus 1160 for outputting information. The output device 1170 may be a visual output device, an audio output device, and/or tactile output device (e.g. vibrations, etc.)

An input device 1175 may be coupled to the bus 1160. The input device 1175 may be an alphanumeric input device, such as a keyboard including alphanumeric and other keys, for enabling a user to communicate information and command selections to processing unit 1110. An additional user input device 1180 may further be included. One such user input device 1180 is cursor control device 1180, such as a mouse, a trackball, stylus, cursor direction keys, or touch screen, may be coupled to bus 1140 through bus 1160 for communicating direction information and command selections to processing unit 1110, and for controlling movement on display device 1170.

Another device, which may optionally be coupled to computer system 1100, is a network device 1185 for accessing other nodes of a distributed system via a network. The communication device 1185 may include any of a number of commercially available networking peripheral devices such as those used for coupling to an Ethernet, token ring, Internet, or wide area network, personal area network, wireless network, or other method of accessing other devices. The communication device 1185 may further be a null-modem connection, or any other mechanism that provides connectivity between the computer system 1100 and the outside world.

Note that any or all of the components of this system illustrated in FIG. 11 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 1120, mass storage device 1130, or other storage medium locally or remotely accessible to processor 1110.

It will be apparent to those of ordinary skill in the art that the system, method, and process described herein can be implemented as software stored in main memory 1120 or read only memory 1150 and executed by processor 1110. This control logic or software may also be resident on an article of manufacture comprising a computer readable medium having computer readable program code embodied therein and being readable by the mass storage device 1130 and for causing the processor 1110 to operate in accordance with the methods and teachings herein.

The present invention may also be embodied in a handheld or portable device containing a subset of the computer hardware components described above. For example, the handheld device may be configured to contain only the bus 1140, the processor 1110, and memory 1150 and/or 1120.

The handheld device may be configured to include a set of buttons or input signaling components with which a user may select from a set of available options. These could be considered input device #1 1175 or input device #2 1180. The handheld device may also be configured to include an output device 1170 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processing unit 1110, a data storage device 1130, a bus 1140, and memory 1120, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 1185.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 1110. A machine-readable medium includes any mechanism for storing information in a form readable by a machine (e.g. a computer). For example, a machine-readable medium includes read-only memory (ROM), random access memory (RAM), magnetic disk storage media, optical storage media, flash memory devices, or other storage media that may be used for temporary or permanent data storage. In one embodiment, the control logic may be implemented as transmittable data, such as electrical, optical, acoustical, or other forms of propagated signals (e.g. carrier waves, infrared signals, digital signals, etc.).

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A system comprising a wristband and a computer system, the wristband comprising:
   an accelerometer;
   a temperature sensor;
   a power management system configured to move the wristband into a low power state reducing a testing frequency when the wristband is not being worn, and to move the wristband into a high power state when the wristband is being worn, the power management system determining when the wristband is worn based on a combination of detected motion from the accelerometer and detected temperature from the temperature sensor indicating that the wristband is being worn;

a communication logic configured to provide data from the accelerometer and the temperature sensor to the computer system;

the computer system including a data merge system configured to merge data to create a unified data set for a user from the wristband and one or more other devices of the user, the data merge system configured to identify conflicting data, indicating two sets of incompatible data covering an overlapping time period, the data merge system configured to identify a correct data set between the two sets by identifying the wristband worn by the user during the time period.

2. The system of claim 1, wherein the temperature sensor comprises a body thermometer configured to be in contact with the user when the wristband is worn, to determine a body temperature.

3. The system of claim 2, the temperature sensor further comprises a second thermometer, and the wristband further comprising a data integration logic configured to calculate a differential between the body temperature measured by the body thermometer and an ambient temperature measured by the second thermometer.

4. The system of claim 1, the wristband further comprising: a band user interface configured to send a notification to the user instructing the user to correct a problem with the temperature sensor when the power management system overrides the temperature sensor.

5. The system of claim 1, the wristband further comprising: a health analysis system configured to determine a recommendation for the user based on the data from the accelerometer and the temperature sensor.

6. The system of claim 5, wherein the health analysis system is further configured to determine an ovulation cycle of a female user based on the detected temperature.

7. The system of claim 1, wherein the communication logic is further configured to receive additional data from one or more additional sensors; and the wristband further comprising a data integration logic configured to integrate the additional data with prior data.

8. The system of claim 1, the wristband further comprising: a sleep analysis logic configured to determine a user's quality of sleep, including receiving temperature data to monitor a user's body temperature and ambient temperature, the sleep analysis logic configured to provide recommendations based on the determination of a user's quality of sleep.

9. The system of claim 8, the communication logic further configured to send a command to an external device to control a user environment, when the sleep analysis logic determines that adjusting the user environment would improve the sleep quality, wherein adjusting the user environment comprises one or more of: increasing or decreasing a temperature, increasing or decreasing noise level, adding white noise, and adjusting an alarm setting.

10. The system of claim 1, the wristband further comprising: a user interface configured to receive an alert of abnormal behavior of the user's body system, wherein the alert comprises a description of the abnormal behavior and a level of probability.

11. The system of claim 1, the wristband further comprising: a user interface to send a notification to the user when the temperature sensor error is identified, wherein the notification requests that the user confirm that the wristband is being worn correctly, the user indicate that the wristband is not being worn, and requesting that the user take the wristband for repairs.

12. A system including a body-worn device, the body-worn device comprising:

a processor;

an accelerometer;

a temperature sensor;

a power management system implemented by the processor configured to move the body-worn device into a low power state when the body-worn device is not being worn by reducing testing frequency and move the body-worn device into a high power state when the body-worn device is being worn, the power management system determining when the body-worn device is worn based on a combination of detected motion from the accelerometer and detected temperature from the temperature sensor indicating that the body-worn device is being worn, the power management system further configured to identify a temperature sensor error when a plurality of measurements of the accelerometer all indicate that the body-worn device is being worn and the temperature sensor indicates that the body-worn device is not being worn, and move the wristband into the high power state;

the body-worn device further comprising a communication logic configured to provide the sensor data to the computer system, from the body-worn device;

a computer system coupled to the body-worn device, the computer system including a data merge system configured to merge data to create a unified data set for a user from the body-worn device and another body-worn device of the user, the data merge system configured to identify conflicting data, indicating two sets of incompatible data covering an overlapping time period, the data merge system configured to identify a correct data set between the two sets by identifying the body-worn device worn by the user during the time period.

13. The system of claim 12, further comprising:

a data integration logic configured to integrate data from a plurality of sensors, the plurality of sensors including the accelerometer and the temperature sensor;

a health analysis system configured to determine a recommendation for a user based on the sensor data, the sensor data including data from the accelerometer and the temperature sensor.

14. The system of claim 12, the body-worn device further comprising:

sleep analysis logic configured to determine a user's quality of sleep, including receiving temperature data to monitor a user's body temperature and ambient temperature, the sleep analysis logic to provide recommendations based on the determination of a user's quality of sleep.

15. The system of claim 14, the communication logic further configured to send a command to an external device configured to control a user environment, when the sleep analysis logic determines that adjusting the user environment would improve the sleep quality, wherein adjusting the user environment comprises one or more of: increasing or decreasing a temperature, increasing or decreasing noise level, adding white noise, and adjusting an alarm setting.

16. The system of claim 12, wherein the data merge system identifies the correct data set based on temperature data from at least one of:
the body-worn device or the another body-worn device.

17. A method of utilizing a body-worn device comprising:
receiving motion data from a first sensor;
receiving temperature data from a second sensor;
controlling a power state of the body-worn device, by moving the body-worn device into a low power state when the body-worn device is not being worn by reducing testing frequency, wherein a determination whether the body-worn device is being worn is made based on a combination of the motion data from the first sensor and the temperature data from the second sensor indicating that the body-worn device is being worn, and wherein moving the body-worn device into a low power state comprises reducing a testing frequency of the temperature sensor;
providing the motion data and the temperature data to a computer system, from the body-worn device;
merging the data to create a unified data set for a user from the body-worn device and another body-worn device of the user, the data merge system configured to identify conflicting data, indicating two sets of incompatible data covering an overlapping time period, the data merge system configured to identify a correct data set between the two sets by identifying the body-worn device worn by the user during the time period.

18. The method of claim 17, further comprising:
integrating data from a plurality of sensors, the plurality of sensors including the accelerometer and the temperature sensor;
determining a recommendation for a user based on the sensor data, the sensor data including data from the accelerometer and the temperature sensor, the recommendation enabling management of a chronic condition.

19. The method of claim 17, further comprising:
determining a user's quality of sleep, including receiving temperature data to monitor a user's body temperature and ambient temperature, the sleep analysis logic to provide recommendations based on the determination of a user's quality of sleep.

20. The method of claim 19, further comprising:
sending a command to an external device to control a user environment when the sleep analysis logic determines that adjusting the user environment would improve the sleep quality, wherein adjusting the user environment comprises one or more of:
increasing or decreasing a temperature, increasing or decreasing noise level, adding white noise, and adjusting an alarm setting.

* * * * *